United States Patent [19]

Suc et al.

[11] Patent Number: 5,417,755
[45] Date of Patent: May 23, 1995

[54] AMPHOTERIC STARCH CONTAINING CARBOXYL AND CATIONIC GROUPS

[75] Inventors: Sophie Suc, Oullins; Jacques Defaye, Saint Ismier; Andrée Gadelle, Montbonnot Saint Martin; Jacques Kervennal, Lyon, all of France

[73] Assignee: Elf Atochem, S.A., Paris, France

[21] Appl. No.: 262,898

[22] Filed: Jun. 21, 1994

Related U.S. Application Data

[63] Continuation of Ser. No. 35,362, Mar. 22, 1993, Pat. No. 5,383,964.

[30] Foreign Application Priority Data

Mar. 23, 1992 [FR] France .................. 92 03465

[51] Int. Cl.[6] .............................................. C08L 3/02
[52] U.S. Cl. .................................... 106/210; 106/213; 106/214; 536/105
[58] Field of Search ................. 106/210, 213, 214; 426/661; 536/105

[56] References Cited

U.S. PATENT DOCUMENTS

| | | | |
|---|---|---|---|
| 3,598,623 | 8/1971 | Powers et al. | 106/214 |
| 3,649,624 | 3/1972 | Powers et al. | 106/214 |
| 3,654,263 | 4/1972 | Cescato | 106/213 |
| 3,706,584 | 12/1972 | Cescato | 106/214 |

OTHER PUBLICATIONS

K. M. Reeve and K. M. Dear, "Oxidation With Hydrogen Peroxide and Hydrogen Peroxide", Indus. Chem Lib. vol. 3, pp. 127–134 (1991) [No Month].

"Benzene, Its Derivatives, and Condensed Benzenoid Compounds", Chem. Abtracts, vol. 116, No. 11, Mar. 16, 1992, p. 25.

Copy of French Search Report, dated Dec. 2, 1992.

*Primary Examiner*—Anthony Green
*Attorney, Agent, or Firm*—Finnegan, Henderson, Farabow, Garrett & Dunner

[57] ABSTRACT

An amphoteric starch containing carboxyl and cationic groups characterized in that its carboxyl groups originate from the selective oxidation of the hemiacetal groups of the cationic starch and possibly of the hemiacetal groups of its products of acid hydrolysis. The process for producing the amphoteric starch consists in reacting a cationic starch in aqueous solution with hydrogen peroxide and hydrobromic acid or bromine, so as to oxidize selectively the hemiacetal groups of the cationic starch and, where appropriate, the hemiacetal groups of its products of acid hydrolysis, to give carboxyl groups.

3 Claims, No Drawings

AMPHOTERIC STARCH CONTAINING CARBOXYL AND CATIONIC GROUPS

This is a continuation of application Ser. No. 08/035,362, filed Mar. 22, 1993, now U.S. Pat. No. 5,383,964.

The present invention relates to a process for the oxidation of cationic starches containing terminal reducing groups.

The invention also relates to the novel amphoteric starches, simultaneously containing carboxyl and cationic groups, which can be obtained by this process.

It is known to modify starch chemically.

Thus, the work "Modified Starches: properties and uses" of O. B. Wurzburg, published by C. R. C. Press, Inc., in 1986, refers to processes for the oxidation of starch by bromine, chlorine or the corresponding alkali metal hypohalites. These reagents oxidise starch in a non-selective manner, and very generally it is accepted that:
- the primary hydroxyl groups in the C-6 position can be oxidised to carboxyl groups, leading to uronic acid units;
- the secondary hydroxyl groups in the C-2, C-3 and C-4 position can be oxidised to ketones;
- the alpha-glycol groups can be oxidised to dialdehydes by oxidative rupture of the C—C bond, and thereafter be oxidised to dicarboxylic derivatives; and
- the hemiacetal groups of amylose and amylopectin are oxidised to carboxyl groups or to lactones.

Thus, I. I. Kuznetsova and N. N. Tregubov, Sakh. Promst., 1984, 9, 47–50 have reacted a corn starch with hydrogen peroxide (0.1% by weight relative to the starch) and hydrochloric acid (0.15% by weight relative to the starch) at temperatures of between 140° and 180° C., by infra-red heating for a period of between 2 and 10 minutes.

According to these authors, the amount of carboxyl groups formed is between 0.003 and 0.006% at 140° C., 0.005 and 0.020% at 160° C. and 0.007 and 0.050% at 180° C. This oxidation is not selective because it causes the formation of reducing substances (R.S.) whose content varies between 1 and 10%.

Furthermore, L. J. Torneport et al., Die Stärke, 1990, 42, 413–417, describe the oxidation of a potato starch suspension by means of bromine in aqueous solution at pH 7. This process also causes the simultaneous formation of carbonyl groups and carboxyl groups.

A. C. B. Salomonson et al., Carbohydr. Res., 1991, 217, 221–225, have determined, by $^1H$ and $^{13}C$ NMR, the composition of the mixture obtained in the above-mentioned process. These authors have confirmed that carbonyl groups are introduced into the C-2 and C-3 positions of the anhydroglucose units, and that carboxylic acids are formed, without however observing the presence of aldone acids resulting from the oxidation of the terminal reducing group to a carboxylic acid group.

Starch can be subjected to other types of chemical modifications and, as is recorded by R. L. Whistler et al., in Kirk-Othmer edit. "Encyclopedia of Chemical Technology,Starch,1983,21, pp 492–507", starch, being a polyhydroxylic structure, can undergo the reactions characteristic of alcohols, and especially esterification and etherification.

The thus-modified starch derivatives, which are very important commercially, in general have a degree of substitution (DS) of less than 0.1. This DS, though low, produces important changes in the physico-chemical properties of these polymers.

Amongst these substitution derivatives, cationic starches, in particular, are known.

Cationic starches are defined as being starches in which certain hydroxyl groups have been etherified by cationic groups or groups capable of being converted to cationic groups by protonation in acid medium. For example, these substituents can contain tertiary amine groups, or quaternary ammonium groups or sulphonium or phosphonium groups.

U.S. Pat. No. 3,654,263 (C. P. C. International Inc.) describes the general methods for obtaining cationic starches and its teaching is incorporated in the present patent application. Preferably, the cationic starches used as the starting material in the present patent application have a cationic DS or $DS_c$ of between about 0.01 and 0.1.

Certain cationic starches are commercially available and are used industrially, especially in coating compositions for paper manufacture, because they increase retention of pigments and fine constituents, as well as increasing the mechanical resistance (to rupture, bursting and tearing) and the internal cohesion.

Amongst the chemically modified starches, there are also known starches, containing carboxyl and cationic groups, which may be defined as being amphoteric starches which simultaneously contain carboxyl groups ($—CO_2H$) and cationic groups. The carboxyl groups can be formed by oxidation from carbon atoms of the anhydroglucose structural unit.

Thus, U.S. Pat. Nos. 3,598,623 and 3,649,624 (A. E. Staley, Manufacturing Company) describe starches, containing carboxyl and cationic groups, obtained in particular by oxidation of cationic starches of the tertiary amino-ether or quaternary ammonium salt type.

The preparation of the carboxylic starches containing ether-tertiary amine substituents requires in some cases that the starch should first of all be oxidised to give a carboxylic starch, and that thereafter the latter should be etherified by a group which carries a tertiary amine function. In fact, the tertiary amine groups are relatively unstable under the oxidation conditions used to obtain a carboxylic starch.

Examples I to XI of these Staley patents describe the preparation of amphoteric starches with carboxyl and quaternary ammonium salt groups, wherein the alkylation agent is 3-chloro-2-hydroxypropyltrimethylammonium chloride and the oxidising agent is sodium hypochlorite.

The degree of substitution of these starches by the carboxyl groups is referred to as the degree of anionic substitution ($DS_a$).

The degree of substitution by the tertiary ammonium radicals is referred to as the degree of cationic substitution ($DS_c$).

Table I summarises the characteristics of the modified starches obtained in Examples I to XI.

TABLE I

| Starch + ($—CO_2—$, $>N<$) | $DS_a$ ($—CO_2H$) | $DS_c +$ ($>N<$) | $DS_a/DS_c$ |
|---|---|---|---|
| A | 0.029 | 0.016 | 1.8 |
| B | 0.050 | 0.016 | 3.1 |
| C | 0.011 | 0.0148 | 0.74 |
| D | 0.029 | 0.028 | 1.03 |
| E | 0.032 | 0.029 | 1.1 |
| F | 0.050 | 0.029 | 1.7 |

TABLE I-continued

| Starch + (—CO$_2$—, >N<) | DS$_a$ (—CO$_2$H) | DS$_c$ + (>N<) | DS$_a$/DS$_c$ |
|---|---|---|---|
| G | 0.050 | 0.036 | 1.4 |
| H | 0.050 | 0.040 | 1.25 |
| I | 0.038 | 0.029 | 1.3 |
| J | 0.022 | 0.018 | 1.2 |
| K | 0.037 | 0.029 | 1.3 |
| L | 0.026 | 0.029 | 0.89 |
| M | 0.041 | 0.017 | 2.4 |
| N | 0.041 | 0.022 | 1.8 |

The starches C and L, wherein the ratio DS$_a$/DS$_c$ is less than 1, produce a so-called "shock" effect with the pigments used, leading to non-homogeneous, extremely viscous mixtures and consequently are not suitable for papermaking applications.

U.S. Pat. Nos. 3,654,263 and 3,706,584 (C. P. C. International Inc.) describe the oxidation of cationic starches by the action of sodium hypochlorite. This oxidation simultaneously introduces carbonyl and carboxyl groups into the cationic starch molecules whilst reducing their average size, namely their degree of polymerisation (D.P.).

Examples 1 and 2 describe the alkylation of starches by means of 3-chloro-2-hydroxylpropyltrimethylammonium, obtained by reaction of trimethylamine with epichlorohydrin.

The analyses, expressed as percentages by weight of carboxyl groups, make it possible to calculate the in the same manner as in the abovementioned Staley patents.

The characteristics of the amphoteric starches obtained, containing carboxyl and quaternary ammonium salt groups, are summarised in Table II.

TABLE II

| Starch (—CO$_2$—, >N$^+$<) | % by weight of —CO$_2$— groups | DS$_a$ | DS$_c$ | DS$_a$/DS$_c$ |
|---|---|---|---|---|
| 1A | 0.10 | 0.0037 | 0.025 | 0.148 |
| 1B | 0.30 | 0.011 | 0.021 | 0.52 |
| 1C | 0.28 | 0.010 | 0.015 | 0.66 |
| 1D | 0.26 | 0.0096 | 0.019 | 0.50 |
| 2A | 0.18 | 0.0066 | 0.014 | 0.47 |
| 2B | 0.31 | 0.0114 | 0.014 | 0.81 |
| 2C | 0.51 | 0.018 | 0.014 | 1.28 |
| 2D | 0.09 | 0.003 | 0.019 | 0.157 |
| 2E | 0.16 | 0.006 | 0.024 | 0.25 |

The amphoteric starches thus obtained are used in paper coating compositions.

The principal object of the present invention is to define a novel class of amphoteric starches which can in particular be used in papermaking.

Another object is to realise a process for the selective oxidation of the terminal reducing groups of a cationic starch and, where appropriate, of its products of acid hydrolysis, making it possible to obtain these amphoteric starches.

Surprisingly, given the state of the art reported above concerning the oxidation of starch by bromine, the abovementioned objects are achieved, according to the present invention, by a process for the oxidation of a cationic starch containing terminal reducing groups, characterised in that the said cationic starch is reacted, in aqueous solution, with hydrogen peroxide and a halogen-containing compound chosen from amongst hydrobromic acid and bromine, so as to oxidise selectively the terminal reducing groups of the cationic starch and, where appropriate, the reducing groups of its products of acid hydrolysis, to give carboxyl groups.

The term "carboxyl group" denotes the carboxylic acid group (—CO$_2$H) or the corresponding lactone, it being possible for these two structures to be in equilibrium depending on the pH to which the starch, containing carboxyl cationic groups, obtained is exposed.

By treating the aqueous solution after oxidation, especially by addition of an alcohol, a starch, containing carboxyl cationic groups, is isolated in the form of a solid precipitate.

Advantageously, the alcohol is chosen from amongst methanol and ethanol. The solid which precipitates is collected by filtration. The amphoteric starch, containing carboxyl and cationic groups, obtainable by the process according to the invention is characterised in that its carboxyl groups originate from the selective oxidation of the terminal hemiacetal groups of a cationic starch starting material and possibly of the terminal hemiacetal groups Of its products of acid hydrolysis.

It is in fact known that the treatment of natural starches with acids in the presence of water leads to the hydrolysis of the alpha-(1→4) and alpha-(1→6) glycoside bonds in the molecules of natural starches (see Supra in Starch, 1983,21, pp 492–507). This hydrolysis has the effect of increasing the number of terminal reducing groups in the products of acid hydrolysis of the starches.

The cationic starches retain, at least partially, the basic polymeric anhydroglucose structure of the amylose and of the amylopectin of the starch and in particular the susceptibility to acid hydrolysis of the alpha-(1→4) and alpha-(1→6) bonds.

The cationic starches are defined as in the above introduction to the present patent application.

The cationic starches which may be used as the starting material in the process according to the invention must be soluble, or solubilisable, in water, so that the oxidation according to the invention shall be both selective and sufficiently rapid for industrial exploitation.

Advantageously, the process is applied to a cationic starch in which the cationic substituents consist of quaternary ammonium salt groups.

These quaternary ammonium groups are preferably grafted onto the molecules of natural starches by etherification of the free hydroxyl groups by alkylating agents containing a tertiary amine group or a quaternary ammonium salt.

The tertiary amine groups can, after etherification of the starch, be quaternarised in the conventional manner by alkylating products such as methyl iodide or bromide or ethyl or methyl sulphate.

Preferably, the alkylating agents are chosen from amongst 2,3-epoxypropyltrimethylammonium chloride, 2-diethylaminoethyl chloride, their arylamine analogues and heterocyclic amine analogues, the hydrohalides of tertiary amines, such as 3-dibutylamino-1,2-epoxypropane, N-(2,3-epoxypropyl)-piperidine and N-(2,3-epoxypropyl)-N-methylaniline, 2-bromo-5-diethylaminopentane hydrobromide, beta-diethylaminoethyl chloride, beta-dimethylaminoethyl chloride or the products of the reaction of epichlorohydrin or epibromohydrin with tertiary amines or the hydrohalides of tertiary amines, such as trimethylamine and triethylamine, trimethylamine hydrochloride, triethylamine hydrobromide, N,N-dimethyldodecylamine, N, N-dimethylcyclohexylamine, N,N-dimethylaniline, N,N- dimethylbenzylamine, N-methylmorpholine, N-methylpiperidine and N-methylpyrrolidone.

The starches used to obtain the cationic starches can be of any desired origin, provided they contain free hydroxyl groups which can be esterified or etherified.

These starches can advantageously be chosen from amongst the chemically unmodified starches originating from wheat starch, corn starch, and in particular those enriched in amylopectin, rice starch, potato starch, tapioca starch, maranta starch and sorghum starch. These starches can also be chosen from amongst starches modified by partial acid hydrolysis, enzymatic hydrolysis or thermal hydrolysis of the natural starches.

Advantageously, the oxidation process according to the invention is carried out in such a way that the said aqueous reaction solution is kept, during the oxidation, at a pH below 7 or particularly preferentially between 4 and 6.

Preferably, the aqueous reaction solution is kept at a temperature of between 20° and 60° C.

Preferably, the hydrogen peroxide ($H_2O_2$) is present in a molar amount greater than the molar amount of the halogen-containing compound, namely HBr or $Br_2$.

The molar ratio $H_2O_2/Br_2$ is advantageously between 1 and 200.

In the presence of a large excess of hydrogen peroxide relative to the bromine or hydrobromic acid, the latter behave like equivalent means, to the extent that it is known from W. C. Bray et al., J. Am. Chem. Soc., 1928, 50, 1654, that $H_2O_2$ oxidises HBr in aqueous solution to give $Br_a$ in accordance with the equation:

$$H_2O_2 + 2HBr \rightarrow Br_2 + 2H_2O$$

In the process according to the invention, any bromine-containing compound capable of yielding bromine under the action of hydrogen peroxide could replace the addition of HBr or $Br_2$ to the reaction solution.

The molar ratio $H_2O_2/HBr$ is advantageously between 0.5 and 100.

One of the advantages of the process according to the invention resides in the fact that bromine, present in a small amount, selectively oxidises the cyclic hemiacetal group according to the reaction:

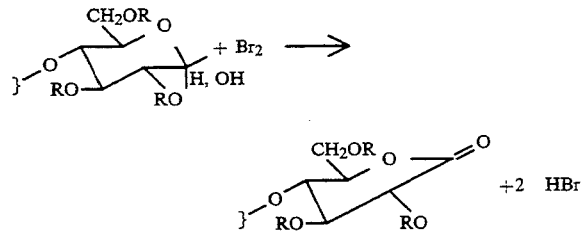

R being statistically a hydrogen atom or, with a low probability at low values of $DS_c$, a cationic substituent.

The hydrobromic acid thus produced is reoxidised, at the rate at which it is formed, by the hydrogen peroxide present in solution.

The low HBr content makes it possible to restrict considerably the hydrolysis of the glycoside bonds alpha-(1→4) and/or alpha-(1→6) of the polymers of the anhydroglucose type.

Advantageously, the molar ratio of hydrogen peroxide to the anhydroglucose units of the cationic starch starting material is between 0.1 and 10.

The present invention will be more readily understood with the aid of the examples which now follow.

The examples of carrying out the process claimed are given purely by way of illustration, whilst the object of the examples of the same process, applied to model compounds, is to demonstrate the selectivity of the oxidation of the cyclic hemiacetal groups in the presence of hydroxyl groups in glucose or anhydroglucose structures of a low degree of polymerisation (DP).

In these examples, the viscosity is measured by means of an AVS 400 apparatus of the company Schott-Gerät, equipped with an UBBELOHDE tube, in dimethylsulphoxide (DMSO).

STA-LOK 180 ® starch from the American company A. E. STALEY has the following characteristics:
  Amylose content: ≦5%
  Amylopectin content: ≧95%
  Cationic nature: quaternary ammonium salt with an ether bond
  % by weight of nitrogen: 0.35
  Degree of cationic substitution, $DS_c$: 0.03
  Viscosity at 3% solids content in water at 66° C.: 286 mPa.s
  Viscosity determined in an UBBELOHDE tube (type 537), on an 0.5% by weight solution in DMSO at 25° C.: $\eta = 40.91$ mm²/s
  Halide content: <250 p.p.m.
  This starch dissolves to an extent of more than 98 g in 100 g of water upon heating to 98° C. followed by cooling.

HI-CAT 180 starch from the company ROQUETTE FRERES has the following characteristics:
  % by weight of nitrogen: 0.6
  Cationic nature: quaternary ammonium salt with ether bond
  Mean degree of polymerisation: not known.
  This starch dissolves in water at ambient temperature.
  UBBELOHDE viscosity (type 537) at 0.25% by weight in DMSO: $\eta = 2.8$ mm²/s The acid content, or content of carboxyl groups, or degree of oxidation, is defined in per cent. It corresponds to the number of carboxyl groups per 100 anhydroglucose units of the modified starch. The degree of substitution is defined as the number of carboxyl groups per 1 anhydroglucose unit of the modified starch.

The hydrogen peroxide and hydrobromic acid are introduced in the form of an aqueous solution of which the strength (for example 30%) expresses the mass in grams of $H_2O_2$ or HBr per 100 grams of solution.

EXAMPLE 1

Oxidation of STA-LOK 180 ® starch and amphoteric starch, containing carboxyl and quaternary ammonium salt groups, thus obtained.

The above starch (5 g) is dissolved in an aqueous hydrogen peroxide solution (30%, 5 ml, 49 mmol, representing 1.6 moles of $H_2O_2$ per anhydroglucose unit of this starch) at the ambient temperature of 20° C., in a reactor equipped with a condenser and a mechanical stirrer. To the viscous solution thus obtained, hydrobromic acid (40% aqueous solution, 0.5 ml, 3.4 mmol) is added all at once, whilst continuing the stirring. After 5 hours, methanol (250 ml) is added to the slightly yellow viscous solution. The precipitate obtained is filtered off and dried to constant weight (5 g, 100%). A potentiometric titration, carried out by adding a sodium hydroxide solution (0.0468N) and noting the inflexion point of the neutralisation curve, makes it possible to determine an acidity content of 0.35%, corresponding to a carboxyl group content or degree of oxidation of 0.15%, representing a degree of substitution $DS_a$ of 0.0015, if one takes account of the residual presence of 0.20% equivalent of ionic bromine $Br^-$, as determined by conductimetry. The proportion of total residual bromine in the sample, determined by argentometry, is 0.46% by weight.

The viscosity of the final product (5 g), determined in an UBBELOHDE tube (type 537) is: $\eta 7.34$ mm$^2$/s on a 0.5% by weight solution.

A microanalysis gives a nitrogen content of 0.36% by weight, corresponding to a $DS_c$ of 0.03.

The ratio $DS_a/DS_c$ is 0.05.

EXAMPLE 2

Under working conditions similar to those of the preceding example, 100 g of the same quaternary ammonium starch are dissolved in a mixture of water (100 ml) and a hydrogen peroxide solution (30% strength, 15 ml, 147 mmol, corresponding to 0.24 mol of oxidant per anhydroglucose unit of the starch), at an ambient temperature of 20° C. To the viscous solution thus obtained, hydrobromic acid (40% aqueous solution, 1.5 ml, 10.2 mmol) is added all at once, whilst continuing the stirring. After 5 hours, the viscous solution is concentrated in vacuo at 30° C. for 0.5 hour. Methanol (500 ml) is added to the residue obtained. The precipitate obtained is filtered off and dried to constant weight (100 g, 100%). A potentiometric titration, carried out by adding a sodium hydroxide solution (0.0468N) makes it possible to determine an overall acidity content of 0.12–0.15%, representing a degree of oxidation of 0.12–0.15%, the overall bromine content being 800 ppm.

Viscosity: $\eta = 12.6$ mm$^2$/s for an 0.5% solution in DMSO $DS_a = 0.0012$–$0.0015$ Microanalysis: 0.37% by weight of nitrogen, corresponding to a $DS_c$ of 0.03

$DS_a/DS_c = 0.04$–$0.05$

EXAMPLE 3

Oxidation of HI-CAT 180 starch (from the company Roquette Frères).

In an apparatus similar to that of Example 1, the above starch (20 g) is dissolved in a mixture of water (20 ml) and a hydrogen peroxide solution (30%, 3 ml, 29.4 mmol, corresponding to 1.24 moles of oxidising agent per anhydroglucose unit of this starch), at an ambient temperature of 20° C. To the very viscous solution obtained, hydrobromic acid (40% solution, 0.3 ml, 2.04 mmol) is added all at once, whilst continuing the stirring. After 5 hours, the very viscous solution is evaporated in vacuo for 0.5 hour, after which methanol (500 ml) is added to the residue thus obtained. The precipitate obtained is filtered off and dried to constant weight (19 g, 95%). A potentiometric titration with sodium hydroxide (0.0468N) makes it possible to determine an acidity content of $1.6 \times 10^{-3}$, corresponding to a carboxyl group content of $1.6 \times 10^{-3}$, representing a $DS_a$ of $1.6 \times 10^{-3}$ if one takes account of the residual presence of 800 ppm of bromine.

Viscosity: $\eta = 3.73$ mm$^2$/s for a 0.25% by weight solution in DMSO.

In order to support the fact that the process according to the present invention selectively oxidises the hemiacetal groups of the cationic starches or of their products of acid hydrolysis, without affecting the primary or secondary hydroxyl groups of the anhydroglucose units, the same oxidation working conditions were applied to model compounds having a glucose structure or formed from anhydroglucose units of a low degree of polymerisation.

EXAMPLE 4

Oxidation of D-glucose to D-gluconic acid

D-glucose (10 g, 55 mmol) is dissolved in a closed chamber (500 ml screw-top bottle) in an aqueous hydrogen peroxide solution (30%, 5 ml, 49 mmol), using a magnetic stirrer, at an ambient temperature of 20° C. Hydrobromic acid (40% aqueous solution, 2 ml, 13.6 mmol) is added all at once whilst continuing the stirring. After 24 hours, an aqueous hydrogen peroxide solution (70%, 2.5 ml, 68 mmol) is added and the reaction is continued for a further 24 hours. Thereafter, water (25 ml) is added to the solution obtained, which is freed from residual bromine by bubbling air through it, before calcium hydroxide (2 g) is added; the mixture is heated and concentrated under reduced pressure to a volume of about 20 ml. The calcium gluconate which crystallises spontaneously from the solution after a few hours is filtered off and recrystallised from water. 11 g (92%) of a product having the following characteristics are obtained:

$[\alpha]_D^{20°} = +8.5°$ (c=3, water) $^{13}$C NMR (D$_2$O, pH=7, (CH$_3$)$_2$CO,delta=31.07) 178.7 (C-1); 74.4; 72.6; 71.3; 70.9 (C-2 to C-5); 62.7 (C-6).

By way of comparison, the literature gives the following values for D-gluconic acid:

$[\alpha]_D^{20°} = +8.5°$, Hudson and Isbell, J. Am. Chem. Soc.,1929,51, 2225 $^{13}$C NMR: (pH 14) 179.8 (C-1); 75.2; 73.8; 72.4; 72.0 (C-2 to C-5); 63.6 (C-6) Isbell, Carbohydr. Res., 1981,90, 123.

EXAMPLE 5

Oxidation of maltose to maltobionic acid isolated in the form of its brucine salt Use precautions are taken in respect of the toxicity of brucine.

Hydrobromic acid (40% aqueous solution, 0.25 ml, 0.17 mmol) is introduced into a closed chamber (100 ml) containing maltose (5 g, 13.9 mmol) dissolved in an aqueous hydrogen peroxide solution (70%, 2.5 ml, 68 mmol). The solution, protected from light, is left with stirring. After 24 hours, an aqueous H$_2$SO$_2$ solution (70%, 2.5 ml, 68 mmol) and hydrobromic acid (40% by weight aqueous solution, 0.25 ml, 0.17 mmol) are added.

After 48 hours, a $^{13}$C NMR spectrum taken on an aliquot portion of the reaction mixture makes it possible to establish that at least 85% of the starting maltose has been converted to maltobionic acid (comparison of the intensities of the peaks at 99.8 (C-1) for maltose and at 100.2 and 100.6 (C-1) for the oxidation product). The residual bromine is removed by bubbling air through the solution, after which water (20 ml) and brucine (6 g, 13.9 mmol) are added. The brucine salt crystals are filtered off (8.2 g, 75%), melting point=151° C., $[\alpha]_D = +33°$ (c=1,3; H$_2$O).

By way of comparison, the literature (Carbohydrate, P. M. Collins edit., Chapman 1987) gives the following characteristics for brucine maltobionate:

melting point=153° C., $[\alpha]_D^{20°} = +38.1°$ (H$_2$O).

This example shows that if acid hydrolysis of the glucoside bond takes place, such hydrolysis is slight, according to the $^{13}$C NMR.

EXAMPLE 6

Oxidation of maltodextrins to polyhydroxycarboxylic acids

The maltodextrins used have a mean degree of polymerisation ($DP_m$) of 5 and originate from the hydrolysis of a starch. They are marketed under the name "Glucidex 19" by the company Roquette Frères (France).

Maltodextrins (5 g, 31 mmol of anhydroglucose corresponding to 5.8 milliequivalents of dextrose) and hydrobromic acid (40% aqueous solution, 0.25 ml, 0.17 mmol) are introduced into a closed chamber (100 ml) containing a hydrogen peroxide solution (70%, 2.5 ml, 68 mmol). The very viscous solution is stirred magnetically, with exclusion of light, for 96 hours at 20° C. An aliquot portion is then taken and analysed by $^{13}$C NMR in comparison with the starting material. The progress of the oxidation reaction is observed as in Example 5 above.

Water (25 ml) is then added to the reaction solution, which is neutralised with sodium hydroxide (0.0468N, 172 ml). The lyophilised product (5.6 g) is washed with methanol, filtered off, redissolved in water (50 ml) and lyophilised (5.2 g, 100%). Microanalysis indicates that 800 ppm of residual bromine remain.

In conclusion, Examples 4, 5 and 6 show clearly that the oxidation reaction claimed is selective for only the hemiacetal reducing groups and that the primary or secondary hydroxyl groups present on the structures in question are not reactive under these conditions.

This selectivity is probably due to the low concentration of bromine in the reaction mixtures formed according to the process of the present invention and to the fact that the oxidising potential of bromine is suitable for the selective oxidation of the hemiacetal group which, by nature, is in equilibrium with the corresponding hydroxyaldehyde structure.

We claim:

1. An amphoteric starch containing carboxyl and cationic groups having a degree of anionic substitution ($DS_a$) between about 0.0012 to 0.0016 formed from a cationic starch starting material having terminal cycles hemiacetal groups by the selective oxidation of said terminal cyclic hemiacetal groups of said cationic starch starting material.

2. The amphoteric starch of claim 1 wherein the cationic starch starting material has a degree of cationic substitution ($DS_c$) between about 0.01 and 0.1.

3. The amphoteric starch of claim 1 containing anhydroglucose units having primary or secondary hydroxyl groups.

* * * * *